United States Patent
Ye et al.

(10) Patent No.: US 11,085,285 B1
(45) Date of Patent: Aug. 10, 2021

(54) METHOD AND APPARATUS FOR PREDICTING DRILLING FLUID VISCOSITY

(71) Applicant: Halliburton Energy Services, Inc., Houston, TX (US)

(72) Inventors: Xiangnan Ye, Cypress, TX (US); Dale E Jamison, Humble, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

(21) Appl. No.: 16/953,140

(22) Filed: Nov. 19, 2020

(51) Int. Cl.
*E21B 44/06* (2006.01)
*G01N 11/10* (2006.01)
*E21B 21/08* (2006.01)
*G01N 33/28* (2006.01)

(52) U.S. Cl.
CPC .............. *E21B 44/06* (2013.01); *E21B 21/08* (2013.01); *G01N 11/10* (2013.01); *G01N 33/2823* (2013.01); *E21B 2200/20* (2020.05)

(58) Field of Classification Search
CPC .......... E21B 44/00; E21B 44/06; E21B 21/08; E21B 47/00; G01N 11/10; G01N 33/2823
See application file for complete search history.

(56) References Cited

U.S. PATENT DOCUMENTS

| | | | |
|---|---|---|---|
| 2003/0029640 A1* | 2/2003 | Cooper | E21B 49/003 175/40 |
| 2016/0102547 A1* | 4/2016 | Ochoa | E21B 47/107 73/152.58 |
| 2017/0274333 A1* | 9/2017 | Smith | B01F 15/00389 |
| 2019/0049361 A1* | 2/2019 | Jennings | G01N 19/00 |
| 2019/0346389 A1* | 11/2019 | Gayrard | G01N 11/10 |
| 2021/0017847 A1* | 1/2021 | Aragall | E21B 21/08 |

\* cited by examiner

*Primary Examiner* — Tara Schimpf
(74) *Attorney, Agent, or Firm* — McGuireWoods LLP

(57) ABSTRACT

A system and method for acquiring and processing single point viscosity measurements in well operations to predict flow curves, e.g., for mud flow, for monitoring and predicting viscosity of fluid flow in order to identify abnormal conditions for taking remedial action.

22 Claims, 5 Drawing Sheets

METHOD AND APPARATUS FOR PREDICTING DRILLING FLUID VISCOSITY

TECHNICAL FIELD

This disclosure relates, in general, to monitoring and prediction of mud rheology for well operations, and more particularly, to monitoring and prediction of mud rheology for well operations including in real-time at downhole conditions at high temperature and pressure for prediction of mud viscosity, among other features.

BACKGROUND

Without limiting the scope of the present disclosure, its background will be described with reference to an environment used for preparation of wells for producing fluid from a hydrocarbon bearing subterranean formation, as an example. Natural resources, such as oil or gas, residing in a subterranean formation can be recovered by drilling a wellbore that penetrates the formation. A variety of fluids can be used in both drilling and completing the wellbore and in resource recovery. Example fluids include drilling fluids, also called mud, that may be pumped into the wellbore during drilling and similar operations may be used to enhanced oil or natural gas recovery.

During the completion of a well that traverses a hydrocarbon bearing subterranean formation, or during downhole cleaning operations, changes in content or character of fluid flow can have impacts on efficiencies or safety of the operations. Event detection of fluid density or viscosity changes are useful to alert operators for monitoring or for altering operational parameters, such as, e.g., drilling speed, for improved safety or increased production.

Improved real time detection and prediction of drilling fluid viscosity during well operations such as for forecasting normal drilling fluid viscosity at operating conditions, or alerting operations management when abnormal drilling fluid viscosity has been detected, is beneficial to overall well drilling operations, such as for taking corrective actions.

BRIEF DESCRIPTION OF THE DRAWINGS

For a more complete understanding of the features and advantage of the present disclosure, reference is now made to the detailed description along with the accompanying figures in which corresponding numerals in the different figures refer to corresponding parts and in which.

DETAILED DESCRIPTION

Figure 1:
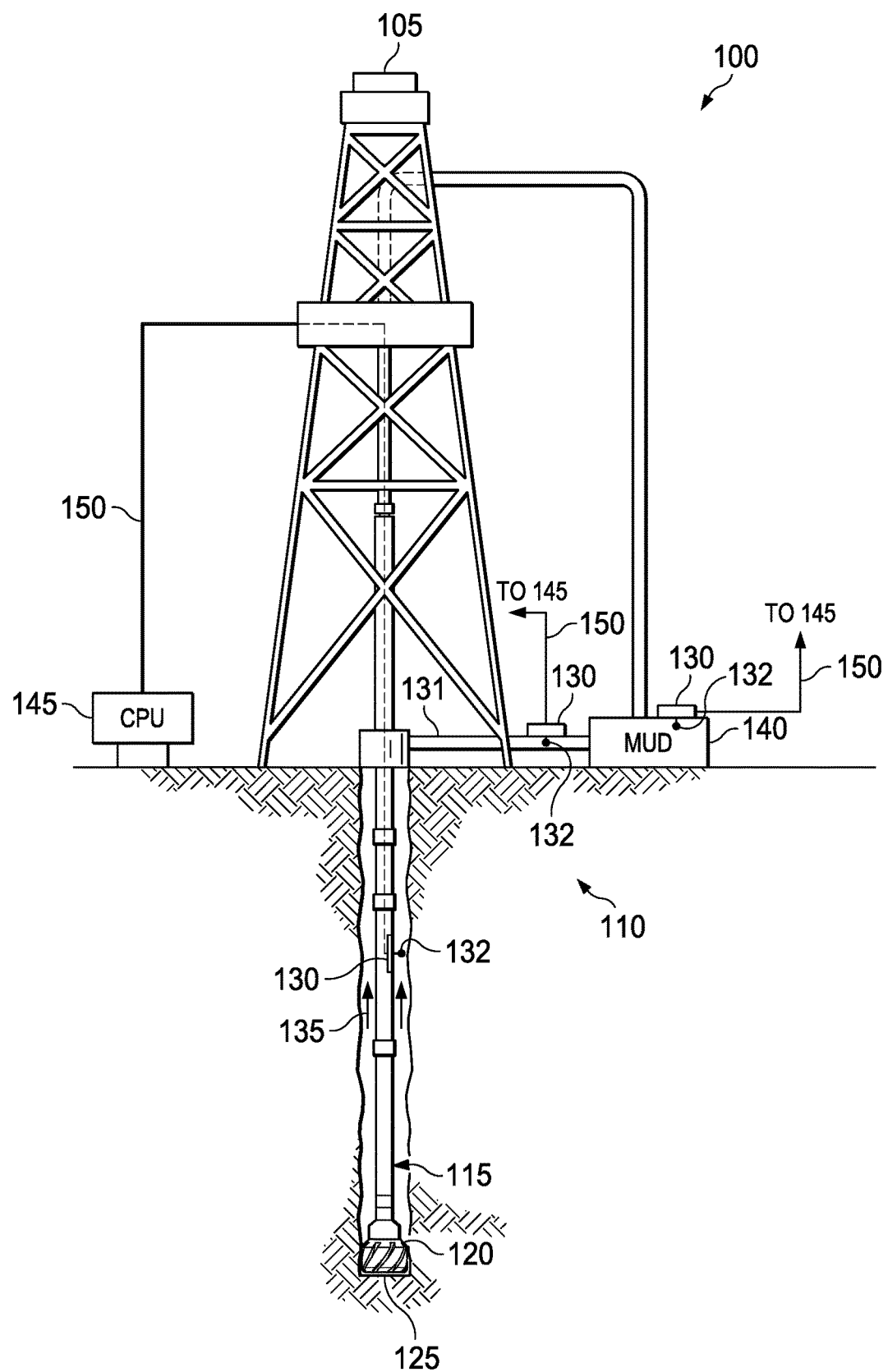
FIG. 1 is a general illustration of an example wellbore drilling system employing real time viscosity detection and prediction, according to principles of the present disclosure.

In the following detailed description of the illustrative embodiments, reference is made to the accompanying drawings that form a part hereof. These embodiments are described in sufficient detail to enable those skilled in the art to practice the disclosed subject matter, and it is understood that other embodiments may be utilized and that logical structural, mechanical, electrical, and chemical changes may be made without departing from the spirit or scope of the disclosure. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

As used herein, the singular forms "a", "an," and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

Unless otherwise specified, any use of any form of the terms connect, engage, couple, attach, or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to." Downhole refers to a direction towards the end or bottom of a well. Uphole refers to a direction generally towards the top of a well or towards the surface.

This disclosure describes a process and system to obtain a whole flow curve (viscosity profile) using a single point viscosity measurement from a resonate sensor for drilling muds. The resonant sensor employed herein may be used at high temperature, high pressure (HTHP) that meets most of the onshore and offshore drilling activities, the process and system herein provides HTHP viscosity measurements for drilling fluids and provides robustness and instant measurement for real time monitoring of the viscosity of drilling fluids.

Drilling muds are a mixture of different additives for improving the drilling fluid specific characteristics. The viscosity of mud is one of the important factors to be monitored and maintained during an entire drilling activity. Typically, drilling fluid is subjected to a wide range of shear in the circulating cycle, with extremely low shear rate in the mud pit, the relatively high shear rate in the drill string, very high shearing through the drill bit at downhole condition, then relative low shear rate in an annulus for coming back to surface. Shear rate refers to the rate of change of velocity at which one layer of fluid passes over an adjacent layer.

Monitoring mud rheological in real-time at downhole conditions such as high temperature, high pressure (HTHP) is a significant advantage of the system described herein. The typical protocols for well operations usually recommend testing the viscosity of mud at 120° F. for water based muds (WBMs) and 120° F. or 150° F. for oil-based muds (OBMs). These rheological data can then be scaled with consideration of the pressure and temperature effects to estimate the mud viscosity at downhole conditions.

Oil-based mud is a drilling fluid used in drilling engineering typically comprising oil as the continuous phase and water as the dispersed phase in conjunction with emulsifiers, wetting agents and gellants. The oil base may be diesel, kerosene, fuel oil, selected crude oil, mineral oil, or the like. Oil-based mud (OBM), a non-newtonian fluid, is known for its superior performance in drilling complex wells as well as combating potential drilling complications. However, the good performance may degrade under certain circumstances especially because of the impact of chemical instability at an elevated temperature. The same phenomenon occurs for water-based mud (WBM) when it is used in drilling under high temperature conditions. The most common weighting material is barite, but others may be used, as is known in the art, e.g., nanosilica nanoparticles, hematite or calcium carbonate.

A typical water-based drilling mud contains a clay, usually bentonite, to give it enough viscosity to carry cutting chips to the surface, as well as a mineral such as, e.g., barite (barium sulfate) to increase the weight of the column enough to stabilize a borehole. The water-based drilling mud can contain other compounds, e.g., nanosilica particles, in lieu of or in addition to clay, as is known in the art. Barite increases the hydrostatic pressure of the drilling mud allowing it to compensate for high-pressure zones experienced during drilling. The softness of the mineral also prevents it from damaging drilling tools during drilling and enables it to serve as a lubricant.

Example functions of drilling fluids includes, but not limited to, providing hydrostatic pressure to prevent formation fluids from entering into the well bore, keeping the drill bit cool and clean during drilling, carrying out drill cuttings, and suspending the drill cuttings while drilling is paused and when the drilling assembly is brought in and out of the hole. The drilling fluid used for a particular job is selected to avoid formation damage and to limit corrosion.

FIG. 1 is a general illustration of an example wellbore drilling system 100 employing real time viscosity detection and prediction, according to principles of the disclosure. FIG. 1 is just one example of a wellbore drilling system configuration, and other configurations may be possible, as one skilled in the art would recognize. An illustrative drilling derrick 105 is shown configured to perform drilling operations, in this example, drilling a well bore 125 in subterranean formation 110. A drilling string 115 drives a bit assembly 125 creating the wellbore 125. Drilling mud is supplied by a mud source, such as mud tank 140, which is pumped to the drilling string 115 with the mud flowing 135 back uphole in the wellbore 125 to the mud tank 140 for recovery via conduit 131. The mud flow 135 illustrates a type of drilling fluid flow that flows in a flow path downhole and/or at the surface 142.

The resonate sensor 130 for measuring fluid density and viscosity may also measure temperature. In applications, the resonate sensor 130 may be located or attached to any portion of the mud flow path within the wellbore or at the surface, as long as the resonate sensor 130 has operational contact via portion 132, comprising a torsional resonator, with the mud flow in real-time. There may be only one resonate sensor 130 deployed in an application, either downhole or at the surface. In other applications, a plurality of resonate sensors 130 may be deployed in a drilling fluid flow path at the surface, in the wellbore or both at the surface and in the wellbore. By using two or more sensors, changes in the rheology of the fluid caused by formation 110 fluid influx into the well system can be measured. In some cases, the viscosity increase due to solids build up due to the wear and tear on the cutting flowing uphole can be detected. These are two forms of event detection. Additionally the resonate sensors 130 provide the ability to model the fluid rheology continuously, and enable better downhole predictions with temperature and pressure.

The resonate sensor 130 may be in communication with the CPU platform 145 located at the surface 142. The CPU platform 145 may comprise a computer having a memory and software for receiving data from the resonate senor 130 and for processing the received data in real-time, as described more below. The CPU platform 145 may be a server and may be in wired or wireless communication with a remote processing platform, such as over a network. The CPU platform 145 may comprise a BaraLogix® Density Rheology Unit (DRU) with associated software. BaraLogix® is a registered trademark of Halliburton Corporation.

The resonate sensor 130 is shown positioned downhole and positioned along a drilling string, however, one or more resonate sensors 130 may be positioned at any suitable position or positions in the mud flow path, including, but not limited to: in-line, attached to an annulus, any conduit carrying the mud either downhole or at the surface, at a downhole tool, or attached to mud tank 140.

Figure 2:
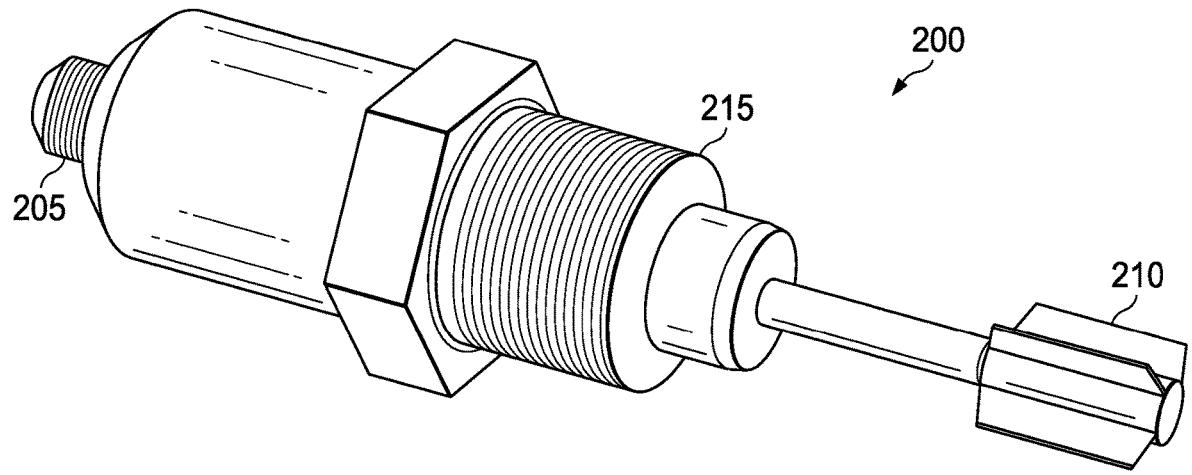
FIG. 2 is an illustration of a resonate sensor for measuring fluid density and viscosity, according to an embodiment of the present disclosure.

FIG. 2 is an illustration of a resonate sensor 200 for measuring fluid density and viscosity, according to an embodiment of the present disclosure. Resonate sensor 200 may be used as the resonate sensor 130 of FIG. 1. An example of a resonate sensor 200, suitable for real-time well operations, is a Rheonics GmbH SRD®. The resonate sensor 200 may comprise a one-point single instrument for simultaneous process density (specific gravity), viscosity and temperature measurement in a compact form-factor for simple installation. The resonate sensor 200 operates in real-time, is stable, providing repeatable and reproducible measurements in Newtonian & non-Newtonian fluids and is capable of measuring kinematic and dynamic viscosity. The resonant sensor 200 may comprise all metal, such as 316L stainless steel, construction and is substantially insensitive to mounting conditions, permitting deployment downhole. The resonant sensor 200 operates to 10,000 psi and 575° F. The resonant sensor 200 may be threaded 215, flanged and sanitary process fittings that are easy to clean, requiring little maintenance or re-configuration.

The resonant sensor 200 may be coupled to, e.g., a conduit, downhole tool, or a tank carrying or passing a mud flow via threads 215, with the bladed portion 210, which is the same as portion 132 of FIG. 1, comprising a torsional resonator, positioned in the mud flow path for obtaining the process density (specific gravity), viscosity and temperature measurement. The communication coupler 205 permits connecting to a communication link 150 for conveying measurements by the resonant sensor 200 to a control unit at the surface such as a central processing unit (CPU) 145 that receives the measurements for real-time processing. CPU 145 may comprise a BaraLogix® Density Rheology Unit (DRU). BaraLogix® DRU is a fully automated unit that can measure the density and rheology of drilling fluids and provides real time wellbore fluid theology and density data. The BaraLogix® DRU comprises a computer processing unit and memory for execution of the software to manage measuring and testing of the density and rheology of drilling fluids and for predicting viscosity of the drilling fluid. The BaraLogix® DRU may include the modeling software described herein and manage the reception of resonator sensor 200 data and perform the real-time modeling for viscosity prediction.

Drilling fluid usually shows shear thinning behavior where its viscosity decreases with increasing shear rate. Several rheological models have been developed to describe the mud viscosity at different shear rates, which is called the flow curve. These include simple power law model that has two model parameters, the most popular Herschel-Bulkley model that has three model parameters, and other complicated models that have more than three parameters. There is one 2-parameter model called the Casson model that has been applied well in oil/gas industry, which will be used in this disclosure for viscosity prediction. However, the principle would be valid as long as the model has two parameters. This disclosure uses the Casson model as an example, but other models may be employed. The Casson model shows:

$$\sqrt{\sigma} = a\sqrt{\dot{\gamma}} + b \quad (1)$$

where $\sigma$ is the shear stress and $\gamma$ is the shear rate. Two model parameters are represented as a and b. For simplicity, the shear stress can use the dial reading of the Fann 35 viscometer and $\gamma$ can be the rotation speed in rpm. Fann 35 viscometer is a laboratory type viscometer for sample testing obtainable from Fann Instrument Company, and is a well-known laboratory test instrument.

Methodology

Flow curves of drilling fluids follow some correlation, especial in the certain shear rate range. For example, the 300 rpm dial reading (of the Fann 35 viscometer) can be expressed as a linear function of the 600 rpm dial reading. This has been observed for extensive muds regardless of mud weight, mud system, temperature as well as oil/water ratio (OWR) etc. Typically, this correlation can be expressed as:

$$\sigma_{300} = 0.587 \times \sigma_{600} \quad (2)$$

where the subscript represents the rotation speed. Combined the Eq. (1) and (2) results in a simple relationship:

$$b = 6.18 \times a \quad (3)$$

The two parameters a and b can be determined as long as one single point viscosity is known.

The resonator sensor 200 measures both viscosity and density by means of a torsional resonator with one end 210, which is immersed in the fluid. The resonator sensor 200 is both excited and sensed by an electromagnetic transducer mounted in the sensor's 200 body. Since the excited frequency is fixed, only a single point viscosity can be measured using this technique. However, it is sufficient for combining in Eq. (3) to determine the model parameters a and b.

Now correlations can be created between the rotational shear stress, shear rate and the resonate sensor 200 signals, which have been determined by the following simple relationships:

$$\dot{\gamma}_{SRD} = 0.85 \times f \quad (4a)$$

$$\sigma_{SRD} = 0.85 \times \tau_{app} \quad (4b)$$

where f is the reported frequency from the resonate sensor 200, $\tau_{app}$ is the apparent stress reported by the resonate sensor 200 by $\tau_{app} = \dot{\gamma}_{SRD} \times \mu_{SRD}$ with $\mu_{SRD}$ the resonate sensor 200 measured viscosity.

Figure 3:
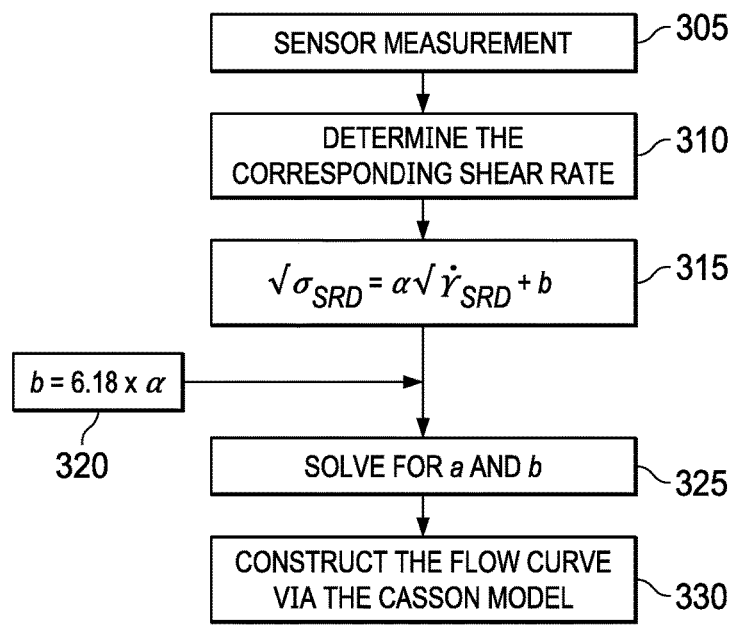
FIG. 3 is a flow chart for determining Casson model parameters, according to principles of the present disclosure.

FIG. 3 is a flow chart for determining Casson model parameters, according to principles of the present disclosure. At step 305, a measurement may be received at the CPU 145 from the resonator sensor 200. At the CPU 145, the corresponding shear rate may be determined at step 310 employing equation (1) and equation (2) at step 315, providing equation (3), denoted as step 320. At step 325, a and b is solved. At step 330, a flow curve may be constructed using the Casson model.

Figure 4:
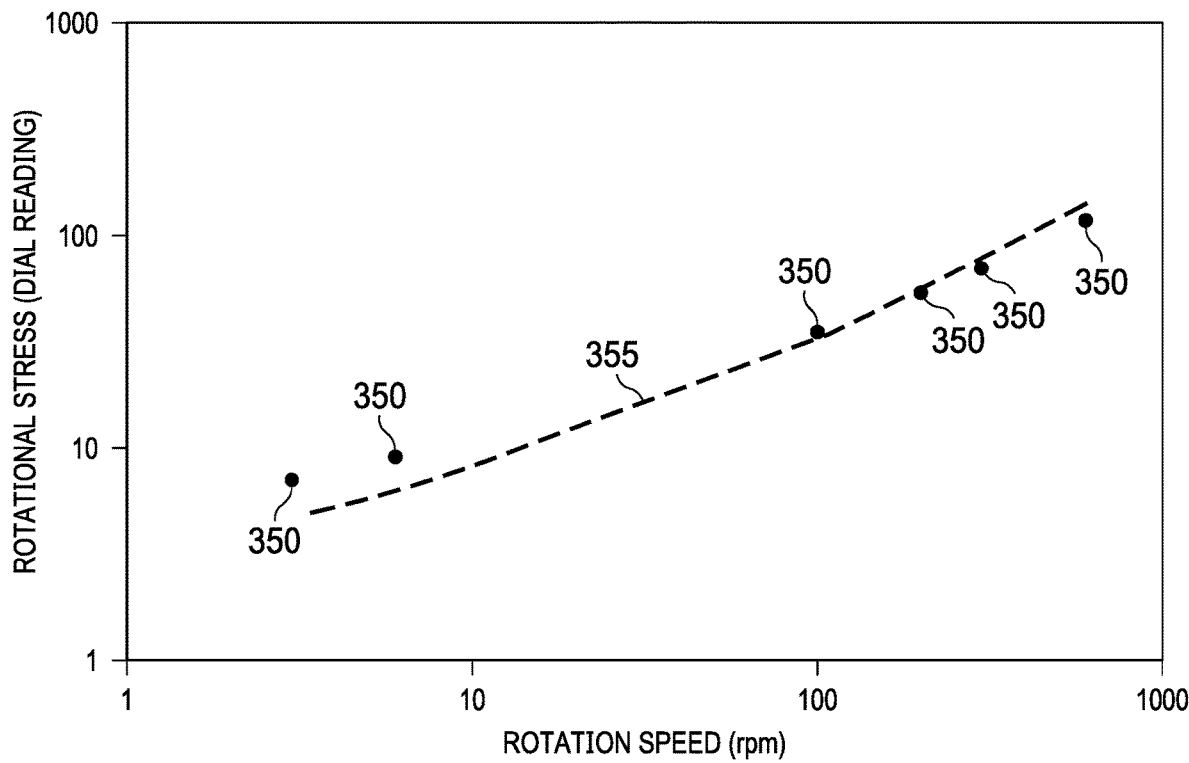
FIG. 4 is a graph illustrating a comparison of laboratory acquired Fann 35 data for oil based muds with 11 ppg and predictions using a real-time system, such as shown, e.g., in FIGS. 1 and 2, according to principles of the present disclosure.

FIG. 4 is a graph illustrating a comparison of laboratory acquired Fann 35 data for oil based muds with 11 ppg mud weight and predictions employing a real-time system, such as shown, e.g., in FIGS. 1 and 2, according to principles of the present disclosure. Measured data from the Fann 35 is shown as dots 350, while predictions employing the resonator 200 is shown as dotted line 315. The rotational stress (y-axis) versus rotation speed (x-axis) correlates quite well between the Fann 35 and the resonator 200 methods, with sufficient prediction accuracy of the resonator 200 measurements as processed by the CPU 145 modeling software to be used in a real-time well operation. The comparison tests were both conducted at 75° F. and atmospheric pressure.

Figure 5:
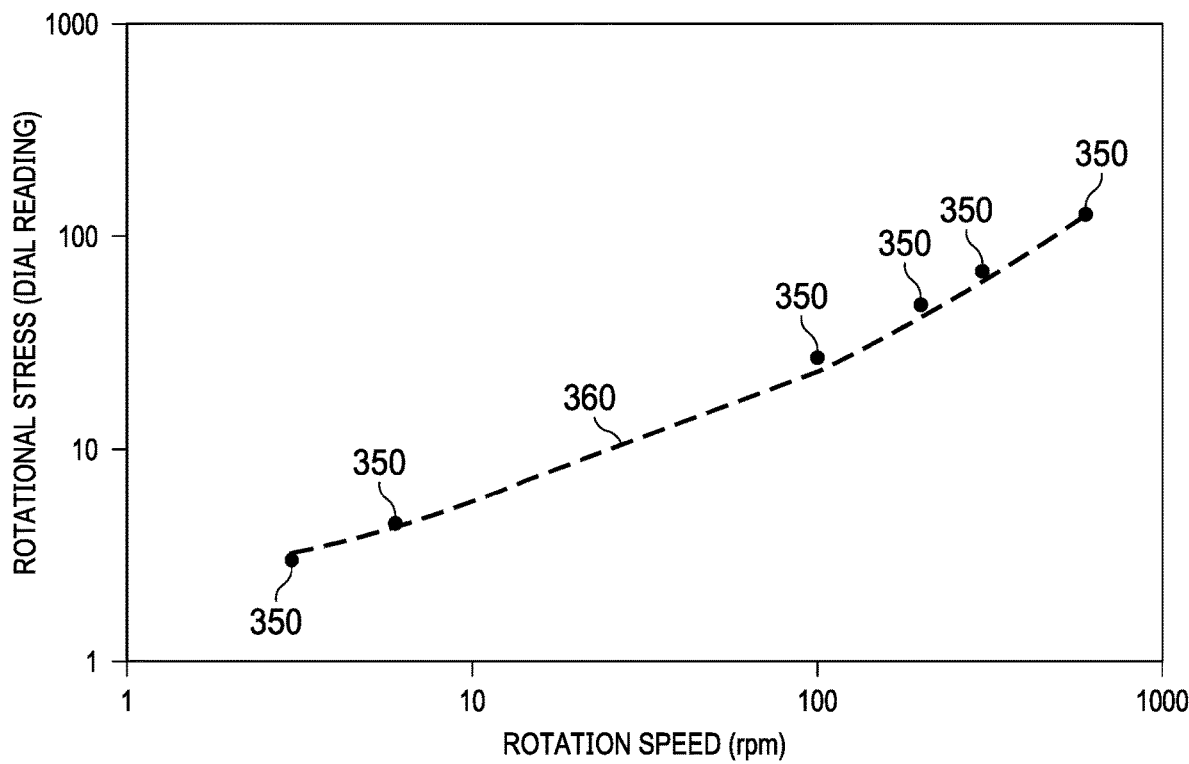
FIG. 5 is a graph illustrating a comparison of laboratory acquired Fann 35 data for oil based muds with 14 ppg and predictions of the same mud using a real-time system, such as shown, e.g., in FIGS. 1 and 2, according to principles of the present disclosure.

FIG. 5 is a graph illustrating a comparison of laboratory acquired Fann 35 data for oil based muds with 14 ppg mud weight and predictions employing a real-time system, such as shown, e.g., in FIGS. 1 and 2, according to principles of the present disclosure. Measured data from the Fann 35 is shown as dots 350, while predictions employing the resonator 200 is shown as dotted line 360. The rotational stress (y-axis) versus rotation speed (x-axis) correlates quite well between the Fann 35 and the resonator 200 methods, with sufficient prediction accuracy of the resonator 200 measurements as process by the CPU 145 modeling software to be used in a real-time well operation. The comparison tests were both conducted at 75° F. and atmospheric pressure.

Figure 6:
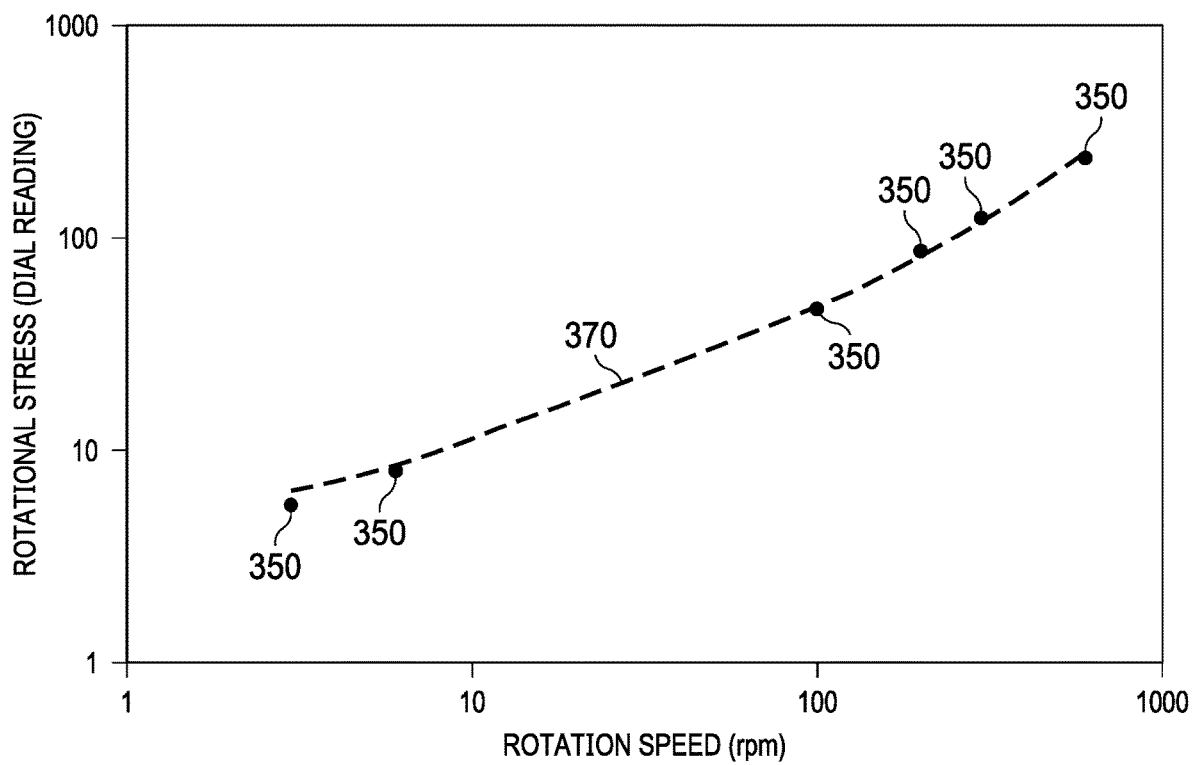
FIG. 6 is a graph illustrating a comparison of laboratory acquired Fann 35 data for oil based muds with 14 ppg and predictions of the same mud using a real-time system, such as shown, e.g., in FIGS. 1 and 2, according to principles of the present disclosure, according to principles of the present disclosure.

FIG. 6 is a graph illustrating a comparison of laboratory acquired Fann 35 data for oil based muds with 17.4 ppg mud weight and predictions employing a real-time system, such as shown, e.g., in FIGS. 1 and 2, according to principles of the present disclosure. Measured data from the Fann 35 is shown as dots 350, while predictions employing the resonator 200 is shown as dotted line 370. The rotational stress (y-axis) versus rotation speed (x-axis) correlates quite well between the Fann 35 and the resonator 200 methods, with sufficient prediction accuracy of the resonator 200 measurements as processed by the CPU 145 modeling software to be used in a real-time well operation. The comparison tests were both conducted at 75° F. and atmospheric pressure.

Figure 7:
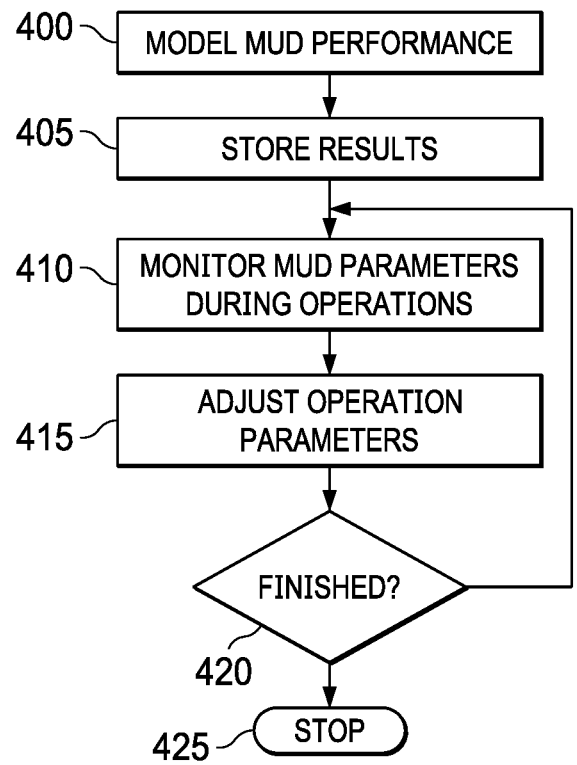
FIG. 7 is a flow chart showings steps of using the wellbore drilling system employing real time viscosity detection and prediction of, e.g., FIGS. 1 and 2, according to principles of the present disclosure.

FIG. 7 is a flow chart showings steps of using the wellbore drilling system employing real time viscosity detection and prediction of, e.g., FIGS. 1 and 2, according to principles of the present disclosure. At step 400, drilling fluid or mud performance may be modeled at various shear rates to develop flow curves. The output of the model may be stored for later recall for comparison in real-time operations. Moreover, as drilling operations occur, the data modeled from a resonator sensor 200 may be stored at step 405 for later recall for comparison and fault detection, e.g., an unsafe operational condition, during well operations. At step 410, the CPU 145 may monitor well operations by receiving real-time information from the resonator sensor 200 of mud parameters including viscosity and density. Mud temperature may also be received by CPU 145. The flow curve of the mud may be generated or constructed by CPU 145. At step 415, a determination as to whether or not an adjustment to operational parameters of the well operation is required, and if needed, operational parameters may be adjusted based on deviations from expected viscosity. The adjustment may be required due to unsafe operational conditions. The operational changes may include, but not limited to: changing drilling speed, increasing or decreasing mud weight concentration, adding or altering additives to the drilling mud, changing drill pipe revolutions per minute (RPM), changing rate of penetration (ROP), changing tripping speeds (surge and swab effects), changing pump rate, changing pressure of drilling mud flow, e.g., higher or lower.

At step 420, a check may be made to determine if the well operation is completed. If not, the process may continue at step 410. If however, well operation is finished, the process ends at step 425.

Figure 8:
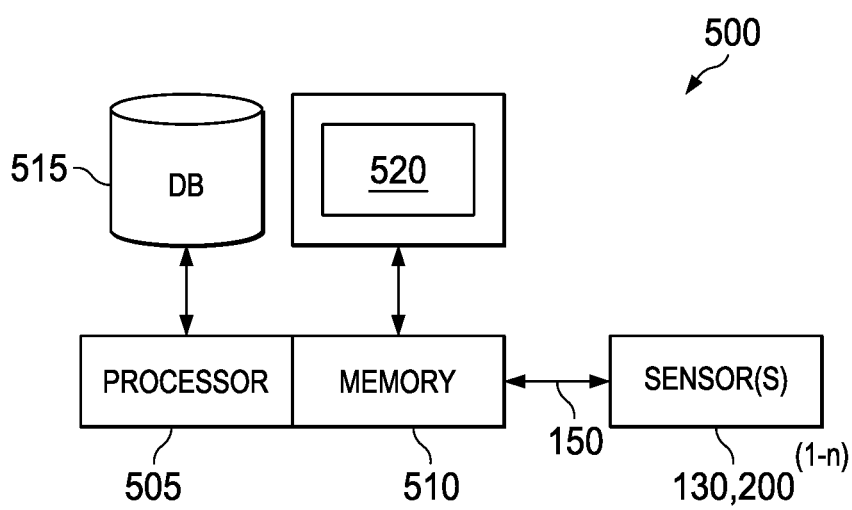
FIG. 8 is an example block diagram of a central processing unit, configured according to principles of the present disclosure.

FIG. 8 is an example block diagram of a central processing unit (CPU) 500 which may be CPU 145 of FIG. 1, configured according to principles of the present disclosure. The central processing unit 500 is used to receive messages and information from one or more resonate sensors 130, 200 during well operations to monitor mud flow conditions and to predict mud viscosity. The CPU 500 comprises a computer processor and software to communicate in real-time with the one or more resonate sensors 130, 200. The CPU 500 may also model flow curves such as, e.g., curves shown in FIGS. 4-6, in real-time for predicting mud flow viscosity. The CPU may employ Casson modeling software in accordance with equations 1-4(b) described herein. The CPU 500 may be in operable communication with a database 515 to store and/or to retrieve the flow curves and related received data, process density (specific gravity), viscosity and temperature, from the resonate sensor 130, 200. The CPU 500 may comprise a BaraLogix® DRU. Results of monitoring the viscosity of mud flow in a mud stream and the modeling of the mud flow using a modeling software that may also run on CPU 500 can be stored in database 515 and displayed on an output device 520. The CPU 500 may also detect deviations from predicted mud flow characteristics and provide suitable notifications to the output device 520 for attention of technicians for making adjustments to operational parameters.

The following clauses provide additional or alternate description in accordance with principles of the disclosure.

Clause 1: A method for predicting drilling fluid viscosity, comprising receiving a single point viscosity measurement of drilling fluid from at least one resonator sensor during a well operation;

generating a flow curve based on the single point viscosity measurement; and adjusting operational parameters of the well operation based on a detected variance from the generated flow curve.

Clause 2: The method of clause 1, wherein the at least one resonator sensor provides real-time viscosity of the drilling fluid.

Clause 3: The method of clause 2, wherein the at least one resonator sensor further provides at least one of: specific gravity, temperature measurement of the drilling fluid.

Clause 4: The method of any one of clauses 1-3, wherein the at least one resonator sensor is positioned to measure drilling fluid in a flow path downhole during a drilling operation Clause 5: The method of any one of clauses 1-3, wherein the at least one resonator sensor is positioned to measure drilling fluid in a flow path downhole during a drilling operation.

Clause 6: The method of any one of clauses 1-5, wherein the flow curve describes mud viscosity at different shear rates.

Clause 7: The method of any one of clauses 1-6, wherein the flow curve is generated using a Casson model.

Clause 8: The method of any one of clauses 1-7, wherein the flow curve is stored in a database for later recall.

Clause 9: The method of clause 1, wherein the at least one resonate sensor comprises a plurality of resonate sensors positioned at different locations in a flow path of drilling fluid to predict viscosity of the drilling fluid at different locations.

Clause 10: The method of any one of clauses 1-9, wherein the step of adjusting operational parameters includes at least one of: i) changing drilling speed, ii) increasing or decreasing mud weight concentration, iii) adding or altering additives to the drilling mud, iv) changing drill pipe revolutions per minute (RPM), v) changing rate of penetration (ROP), vi) changing tripping speeds, vii) changing pump rate and viii) changing pressure of drilling mud flow.

Clause 11: A method for predicting drilling fluid viscosity, comprising:

receiving in real-time a viscosity and a density measurement of drilling fluid from at least one resonator sensor located in-line of drilling fluid flow during a well operation;

adjusting operational parameters of the well operation based on the real-time viscosity and density measurement.

Clause 12: The method of clause 11, wherein the at least one remote sensor measures the viscosity and density using a torsional resonator.

Clause 13: The method of clauses 11 or 12, further comprising generating a flow curve based on viscosity measurement for determining whether or not an adjustment to operational parameters of the well operation is required.

Clause 14: A system for predicting drilling fluid viscosity, comprising:

at least one resonate sensor positioned in a fluid flow in a well operation;

a processing unit to receive a real-time viscosity measurement from the at least one resonate sensor, wherein the processing unit models and generates a flow curve based on the received real-time viscosity measurement for providing information to change in operational parameters of a well operation.

Clause 15: The system of clause 14, wherein the at least one resonate sensor comprises a plurality of resonate sensors positioned at different locations of a fluid flow in a well operation.

Clause 16: The system of claim 14, wherein the at least one resonate sensor is positioned down hole.

Clause 17: The system of clause 14, wherein the at least one resonate sensor is positioned at the surface of the well operation.

Clause 18: The system of any one of clauses 14-17, wherein the at least one resonate sensor and the processing unit communicate over a communication link.

Clause 19: The system of any one of clauses 14-18, wherein the processing unit uses a Casson model to generate the flow curve.

Clause 20: The system of any one of claims 14-19, wherein the processing unit comprises a BaraLogix® Density Rheology Unit (DRU).

The embodiments set forth herein are merely illustrative and do not limit the scope of the disclosure. It will be appreciated that many other modifications and improvements to the disclosure herein may be made without departing from the scope of the disclosure.

We claim:

1. A method for predicting drilling fluid viscosity, comprising:
   receiving a single point viscosity measurement of drilling fluid from at least one
   resonate sensor during a well operation, the at least one resonate sensor located at the surface;
   predicting viscosity of the drilling fluid at different shear rates based on the received single point viscosity measurement for monitoring the drilling fluid rheology in real-time;
   generating a flow curve of the predicted viscosity of the drilling fluid at different shear rates; and
   adjusting operational parameters of the well operation based on a detected variance from the generated flow curve.

2. The method of claim 1, wherein the at least one resonate sensor provides real time viscosity of the drilling fluid.

3. The method of claim 2, wherein the at least one resonate sensor further provides at least one of: specific gravity and temperature measurement of the drilling fluid.

4. The method of claim 1, wherein the at least one resonate sensor comprises a plurality of sensors and at least one of the plurality of sensors is positioned to measure drilling fluid in a flow path downhole during a drilling operation.

5. The method of claim 1, wherein the flow curve is generated using a Casson model.

6. The method of claim 1, wherein the flow curve is stored in a database for later recall.

7. The method of claim 1, wherein the at least one resonate sensor comprises a plurality of resonate sensors positioned at different locations in a flow path of drilling fluid to predict viscosity of the drilling fluid at different locations.

8. The method of claim 1, wherein the step of adjusting operational
   parameters includes at least one of: i) changing drilling speed, ii) increasing or decreasing mud weight concentration, iii) adding or altering additives to the drilling mud, iv) changing drill pipe revolutions per minute (RPM), v) changing rate of penetration (ROP), vi) changing tripping speeds, vii) changing pump rate and viii) changing pressure of drilling mud flow.

9. The method of claim 1, wherein in the receiving step, the at least one sensor comprises a plurality of sensors including a first sensor and a second sensor, the first sensor being at the surface positioned in a fluid flow flowing from a wellbore and the first sensor located between the wellbore and a mud source.

10. The method of claim 9, wherein the second sensor is located in the fluid flow at the surface.

11. The method of claim 10, wherein the plurality of sensors includes a third sensor located in the wellbore, the plurality of sensors to measure changes in the rheology of the fluid flow caused by influx from a subterranean formation.

12. A method for predicting drilling fluid viscosity, comprising:
    receiving in real-time a viscosity measurement and a density measurement of drilling fluid from at least one resonate sensor located in-line of drilling fluid flow during a well operation, the at least one sensor located at the surface;
    predicting viscosity of the drilling fluid at different shear rates based on the viscosity and density measurement for monitoring the drilling fluid rheology in real-time; and
    adjusting operational parameters of the well operation based on the predicted viscosity of the drilling fluid at different shearing rates.

13. The method of claim 12, wherein the at least one resonate sensor measures the viscosity and density using a torsional resonator.

14. The method of claim 12, further comprising generating a flow curve based on the viscosity measurement for adjusting operational parameters of the well operation.

15. The method of claim 12, wherein in the receiving step, the at least one sensor comprises a plurality of sensors including a first sensor and a second sensor, the first sensor being at the surface positioned in a fluid flow flowing from a wellbore, and the first sensor located between the wellbore and a mud source.

16. A system for predicting drilling fluid viscosity, comprising:
    at least one resonate sensor positioned in a fluid flow in a well operation, the at least one sensor located at the surface; and
    a processing unit to receive a single-point real-time viscosity measurement from the at least one resonate sensor, wherein the processing unit models the drilling fluid based on the received single-point real-time viscosity by predicting viscosity at different shear rates for monitoring rheology of the drilling fluid and for providing information to change operational parameters of the well operation.

17. The system of claim 16, wherein the at least one resonate sensor comprises a plurality of resonate sensors positioned at different locations of the fluid flow in the well operation.

18. The system of claim 16, wherein the at least one resonate sensor comprises a plurality of sensors and at least one of the plurality of sensors is positioned down hole.

19. The system of claim 16, wherein the at least one resonate sensor is positioned at the surface of the well operation.

20. The system of claim 16, wherein the at least one resonate sensor and the processing unit communicate over a communication link.

21. The system of claim 16, wherein the processing unit uses a Casson model to generate the flow curve.

22. The system of claim 16, wherein the at least one sensor comprises a plurality of sensors including a first sensor and a second sensor, the first sensor being at the surface positioned in a fluid flow flowing from a wellbore, and the first sensor located between the wellbore and a mud source.

* * * * *